(12) United States Patent
Rentas Torres et al.

(10) Patent No.: US 11,426,596 B2
(45) Date of Patent: Aug. 30, 2022

(54) EMBEDMENT OF MEDICAL LEAD COIL ELECTRODES

(71) Applicant: Medtronic, Inc., Minneapolis, MN (US)

(72) Inventors: Douglas Rentas Torres, Villalba (TR); George W. McFall, Minneapolis, MN (US); William Clemens, Fridley, MN (US); Dina L. Williams, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 95 days.

(21) Appl. No.: 16/453,126

(22) Filed: Jun. 26, 2019

(65) Prior Publication Data

US 2020/0406048 A1 Dec. 31, 2020

(51) Int. Cl.
*A61N 1/39* (2006.01)

(52) U.S. Cl.
CPC .................................. *A61N 1/3956* (2013.01)

(58) Field of Classification Search
CPC .... A61N 1/3956; A61N 1/752; A61N 1/0472; A61N 1/0476; A61N 1/048; A61N 1/0488; A61N 1/0595; A61N 1/36017
See application file for complete search history.

(56) References Cited

U.S. PATENT DOCUMENTS

| | | | |
|---|---|---|---|
| 5,040,544 A | 8/1991 | Lessar et al. | |
| 5,042,143 A * | 8/1991 | Holleman | A61N 1/056 29/825 |
| 5,342,414 A | 8/1994 | Mehra | |
| 5,488,768 A * | 2/1996 | Mar | H01R 43/02 228/904 |
| 5,534,022 A * | 7/1996 | Hoffmann | A61N 1/0563 607/119 |
| 5,609,621 A | 3/1997 | Bonner | |
| 6,016,436 A * | 1/2000 | Bischoff | A61N 1/0565 600/374 |
| 6,464,700 B1 * | 10/2002 | Koblish | A61N 1/056 606/49 |

(Continued)

FOREIGN PATENT DOCUMENTS

EP 0442444 A2 8/1991

OTHER PUBLICATIONS

International Search Report dated Sep. 9, 2020, corresponding to counterpart Application No. PCT/US2020/037851; 3 pages.

(Continued)

*Primary Examiner* — Brian T Gedeon
*Assistant Examiner* — Joshua Andrew Schum-Houck
(74) *Attorney, Agent, or Firm* — Shumaker & Sieffert, P.A.

(57) ABSTRACT

In some examples, a coil electrode assembly includes a coil electrode including a plurality of windings and extending from an electrode proximal end to an electrode distal end, the coil electrode defining an electrode lumen from the electrode proximal end to the electrode distal end. The coil electrode assembly further includes an insulative tube extending within the lumen of the coil electrode such that the coil electrode extends along an outer surface of the insulative tube. The coil electrode is partially embedded within the insulative tube when the insulative tube is in an expanded state to maintain a spacing between the windings.

10 Claims, 8 Drawing Sheets

(56) References Cited

U.S. PATENT DOCUMENTS

| | | | |
|---|---|---|---|
| 7,904,178 B2 | 3/2011 | Williams et al. | |
| 8,396,568 B2 | 3/2013 | Williams | |
| 8,666,511 B2 | 3/2014 | Williams | |
| 2010/0256718 A1* | 10/2010 | Wang | A61N 1/05 607/116 |
| 2016/0144189 A1* | 5/2016 | Bakker | A61B 5/6868 607/45 |
| 2017/0246459 A1* | 8/2017 | Kelley | A61N 1/3956 |
| 2018/0256910 A1* | 9/2018 | Shan | A61N 1/3956 |

OTHER PUBLICATIONS

Written Opinion of the International Searching Authority dated Sep. 9, 2020, corresponding to counterpart Application No. PCT/US2020/037851; 7 pages.

\* cited by examiner

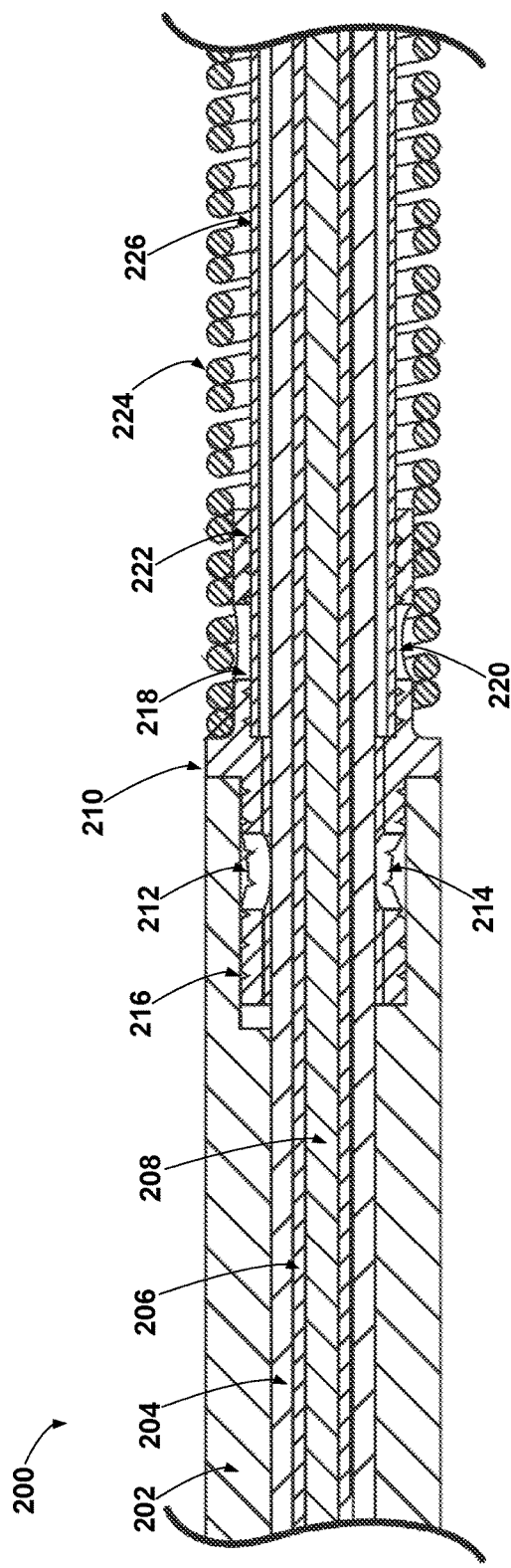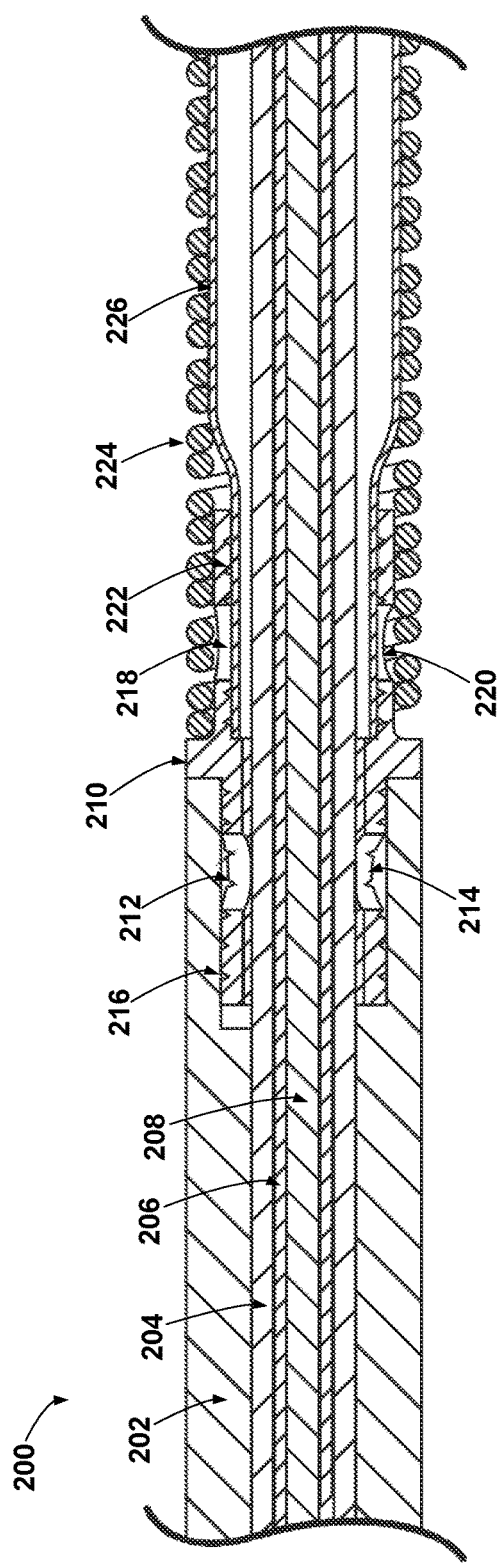

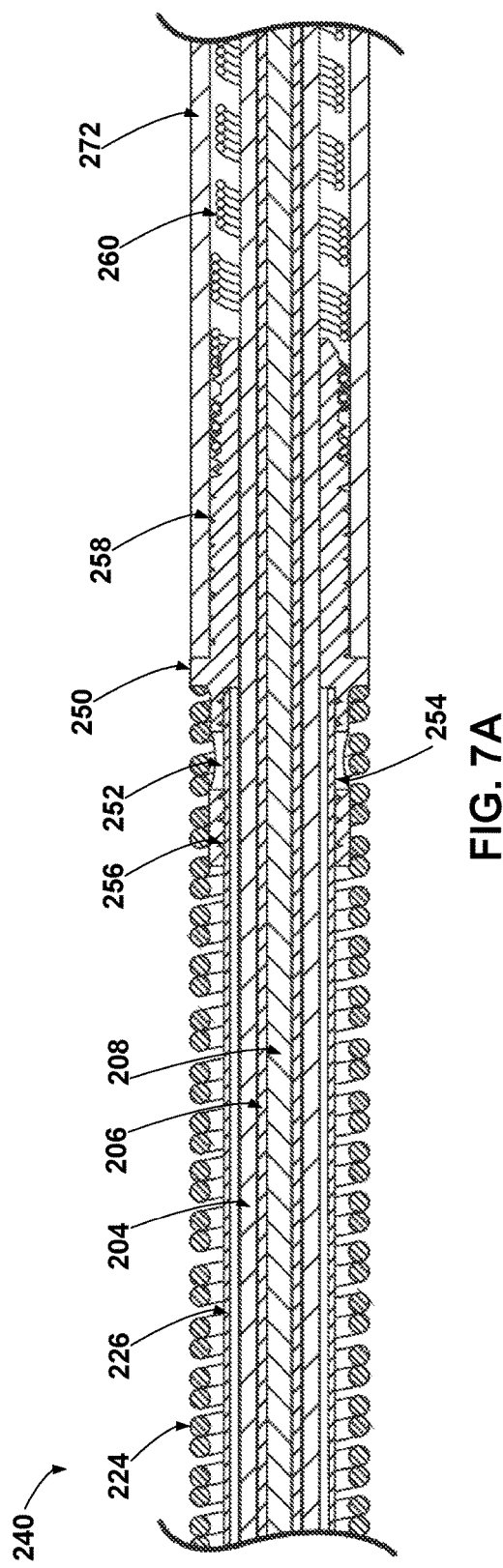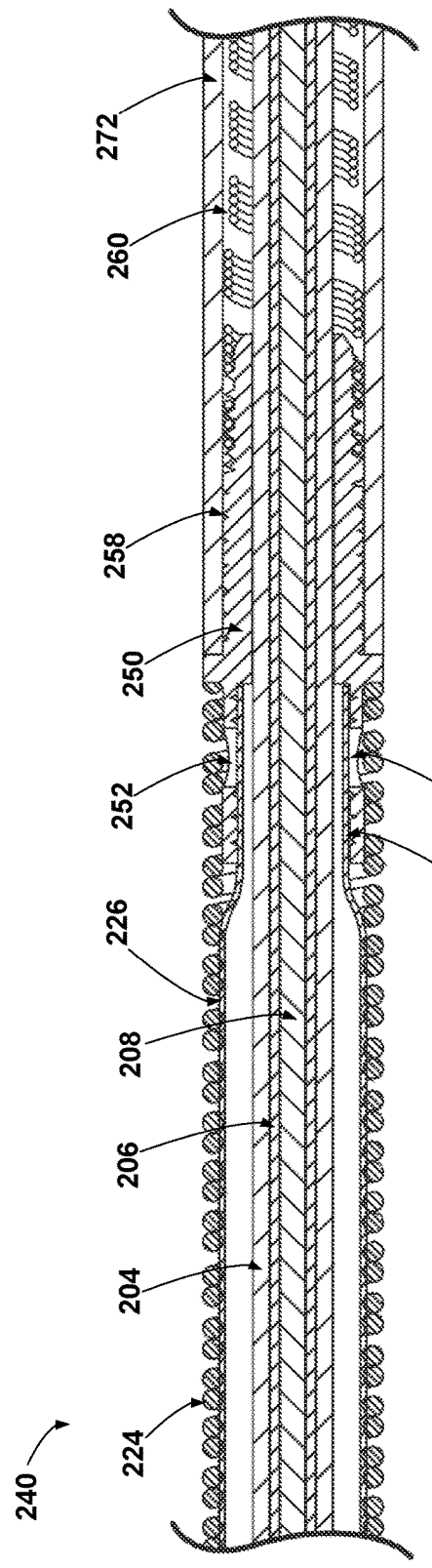
FIG. 7A
FIG. 7B

EMBEDMENT OF MEDICAL LEAD COIL ELECTRODES

FIELD

This disclosure is generally related to implantable medical devices.

BACKGROUND

Implantable medical devices may be used to monitor a variety of conditions of patients and/or to deliver a variety of therapies to patients. Some implantable medical devices include electrodes to sense electrical signals and/or deliver electrical therapies. Some implantable medical devices include elongated leads to position the electrodes proximate to target tissue for sensing or therapy delivery. For example, an implantable medical device may deliver anti-tachyarrhythmia (e.g., defibrillation) shocks via one or more coil electrodes that are part of one or more leads and are located within or proximate to the heart.

SUMMARY

The techniques of this disclosure generally relate to assembling implantable medical leads including coil electrodes and, more particularly, to securing the windings of a coil electrode, e.g., preserving intra-winding spacing, by an "inside-out" approach. In some existing implantable medical leads, coil electrodes are secured using an adhesive applied from the outside of the coil electrode. In contrast, the techniques of the present disclosure secure the coil electrode using an insulative tube disposed within a lumen defined by the coil electrode, which may increase the surface area of the coil electrode available for blood/tissue contact to interact with relative to the existing implantable medical leads.

The insulative tube within the lumen is transitioned to an expanded state to make contact with the coil electrode, e.g., such that the coil electrode is partially embedded within the insulative tube, and thus secure the spacing between the windings. The expansion of the tube may be done through the application of heat and/or air pressure to the inside of the tube. In some examples, prior to expanding the insulative tube, transition rings are connected at the ends of the coil electrode and the tube to maintain them in place relative to one another during expansion of the tube.

In some examples, the coil electrode assembly may be constructed as a subassembly for the implantable medical leads. Making the implantable medical lead using such a subassembly process can help reduce waste, because if one subassembly part needs to be scrapped, the remaining portion of the lead does not need to be scrapped as well. Examples in which the coil electrode assembly includes one or more conductive transition rings may also facilitate electrical connection of the coil electrode to a conductor of the implantable medical lead via the transition ring.

In one example, the present disclosure provides an implantable medical lead configured to be coupled to an implantable medical device, the implantable medical lead comprising a coil electrode assembly. The coil electrode assembly comprises a coil electrode extending from an electrode proximal end to an electrode distal end, the coil electrode defining an electrode lumen from the electrode proximal end to the electrode distal end, and the coil electrode comprising a plurality of windings. The coil electrode assembly further comprises an insulative tube extending from a tube proximal end to a tube distal end, the insulative tube extending within the electrode lumen such that the coil electrode extends along an outer surface of the insulative tube, the coil electrode partially embedded within the insulative tube when the insulative tube is in an expanded state to maintain a spacing between the windings. The coil electrode assembly further comprises a first transition ring at the electrode distal end and the tube distal end, wherein a portion of the first transition ring is within the electrode lumen, wherein the first transition ring defines a first transition ring lumen, and wherein a distal portion of the insulative tube including the tube distal end is within the first transition ring lumen. The coil electrode assembly further comprises a second transition ring at the electrode proximal end and the tube proximal end, wherein a portion of the second transition ring is within the electrode lumen, wherein the second transition ring defines a second transition ring lumen, and wherein a proximal portion of the insulative tube including the tube proximal end is within the second transition ring lumen.

In another example, the disclosure provides a system comprising an implantable medical device configured to generate an antitachyarrhythmia shock, and an implantable medical lead extending from a lead proximal end to a lead distal end, the lead proximal end configured to be coupled to the implantable medical device, the implantable medical lead comprising a coil electrode assembly between the lead proximal end and the lead distal end. The coil electrode assembly comprises a coil electrode extending from an electrode proximal end to an electrode distal end, the coil electrode defining an electrode lumen from the electrode proximal end to the electrode distal end, and the coil electrode comprising a plurality of windings, wherein the coil electrode is configured to deliver the antitachyarrhythmia shock. The coil electrode assembly further comprises an insulative tube extending from a tube proximal end to a tube distal end, the insulative tube extending within the electrode lumen such that the coil electrode extends along an outer surface of the insulative tube, the coil electrode partially embedded within the insulative tube when the insulative tube is in an expanded state to maintain a spacing between the windings. The coil electrode assembly further comprises a first transition ring at the electrode distal end and the tube distal end, wherein a portion of the first transition ring is within the electrode lumen, wherein the first transition ring defines a first transition ring lumen, and wherein a distal portion of the insulative tube including the tube distal end is within the first transition ring lumen. The coil electrode assembly further comprises a second transition ring at the electrode proximal end and the tube proximal end, wherein a portion of the second transition ring is within the electrode lumen, wherein the second transition ring defines a second transition ring lumen, and wherein a proximal portion of the insulative tube including the tube proximal end is within the second transition ring lumen.

In another example, the disclosure provides a coil electrode assembly for an implantable medical lead configured to be coupled to an implantable medical device. The coil electrode assembly comprises a coil electrode extending from an electrode proximal end to an electrode distal end, the coil electrode defining an electrode lumen from the electrode proximal end to the electrode distal end, and the coil electrode comprising a plurality of windings. The coil electrode assembly further comprises an insulative tube extending from a tube proximal end to a tube distal end, the insulative tube extending within the electrode lumen such that the coil electrode extends along an outer surface of the insulative tube, the coil electrode partially embedded within the insulative tube when the insulative tube is in an expanded state to maintain a spacing between the windings. The coil electrode assembly further comprises a first transition ring at the electrode distal end and the tube distal end, wherein a portion of the first transition ring is within the electrode lumen, wherein the first transition ring defines a first transition ring lumen, and wherein a distal portion of the insulative tube including the tube distal end is within the first transition ring lumen. The coil electrode assembly further comprises a second transition ring at the electrode proximal end and the tube proximal end, wherein a portion of the second transition ring is within the electrode lumen, wherein the second transition ring defines a second transition ring lumen, and wherein a proximal portion of the insulative tube including the tube proximal end is within the second transition ring lumen.

In another example, a method comprises inserting an insulative tube within an electrode lumen defined by a coil electrode of a coil electrode assembly such that the coil electrode extends along an outer surface of the insulative tube, the insulative tube extending from a tube proximal end to a tube distal end and the coil electrode extending from an electrode proximal end to an electrode distal end, and the coil electrode comprising a plurality of windings. The method further comprises connecting a first transition ring to the coil electrode at the electrode distal end and to the insulative tube at the tube distal end, and connecting a second transition ring to the coil electrode at the electrode proximal end and to the insulative tube at the tube proximal end. The method further comprises applying at least one of heat and gas pressure to the insulative tube to transition the insulative tube from a non-expanded state to an expanded state such that the coil electrode is partially embedded within the insulative tube and a spacing between the windings is maintained.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 6A and 6B are cross-sectional diagrams illustrating a pre-expansion state and a post-expansion state, respectively, of a region of another example coil electrode assembly similar to region A of the example coil electrode assembly of FIG. 2.

FIGS. 7A and 7B are cross-sectional diagrams illustrating a pre-expansion state and a post-expansion state, respectively, of another region of the other example coil electrode assembly similar to region B of the example coil electrode assembly of FIG. 2.

DETAILED DESCRIPTION

Electrodes used to deliver relatively higher-energy (e.g., compared to cardiac pacing) anti-tachyarrhythmia (e.g., defibrillation) shocks can take the form of a wound coil with the outside surface exposed to the blood or other bodily fluid. The windings of these coils are typically secured in their axial position with respect to the underlying lead body tube and each other (e.g., to avoid filar dislocation, fracture, or fibrosis tissue ingrowth) through depositing silicone adhesive or silicone rubber in an outside-in direction to cover the wound coil and the space between the coils. Due to this deposition of the silicone adhesive or silicone rubber, an exterior surface of wound coil, including the spaces between the electrodes, can be fully or partially covered with a thin coating.

While the thin coating can lock the wound coils in place, preventing movement of the defibrillation coil electrode, the coating may potentially reduce the performance of the coil electrode due to reduced available surface area of the coil electrode. In some examples, in order to counteract the reduction of available surface area of the coil electrode, the excess adhesive is removed from the outer surface of the coil. However, removing the adhesive requires relatively skilled labor and adds a step to the process of making the implantable medical lead including the coil electrode. Also, using conventional lead assembly techniques, errors in the application of the adhesive or the removal of the thin coating may lead to scrapping the entire implantable medical lead.

A coil electrode assembly according to this disclosure includes an insulative tube within a lumen defined by the coil electrode, and the insulative tube is transitioned to an expanded state to partially embed the coil electrode to secure the coil windings in place via an inside-out approach. In this manner, the coil electrode assembly described herein may have increased outer surface area for delivery of anti-tachyarrhythmia shocks. Increasing the available surface areas of the coil can increase the effectiveness of the shock delivered, e.g., during ventricular tachycardia (VT) and ventricular fibrillation (VF). Additionally, manufacturing an implantable medical lead including a coil electrode assembly, as described herein, can reduce operator variability and provide cost savings by creating subassemblies that are to be assembled together to create the final product. For example, if the coil electrode assembly is not assembled correctly, only the coil electrode assembly needs to be scrapped.

Figure 1:
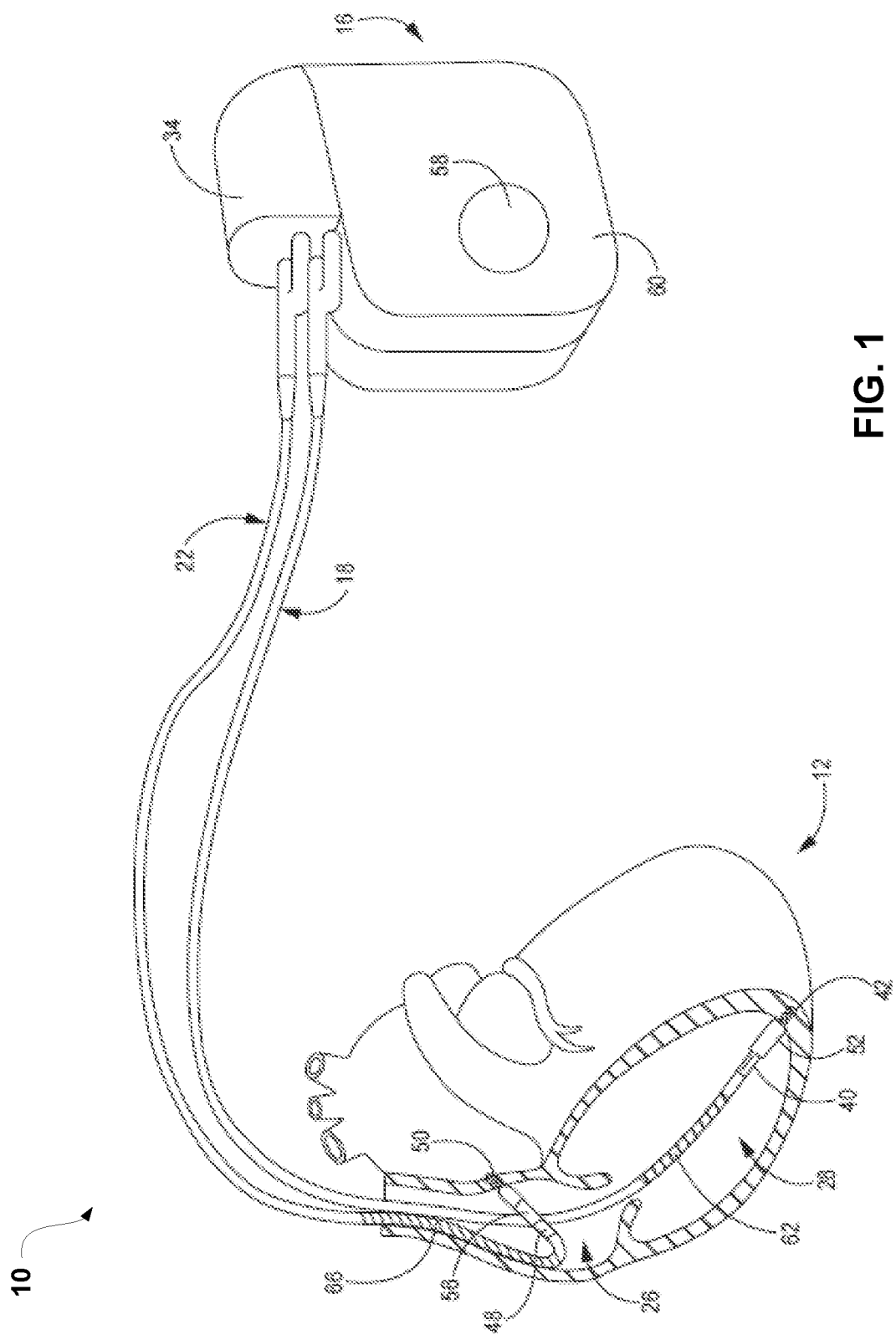
FIG. 1 is a conceptual diagram illustrating an example medical device system including an implantable medical device coupled to one or more coil electrodes on one or more implantable medical leads.

FIG. 1 is a conceptual diagram illustrating an example medical device system 10 including an implantable medical device (IMD) 16 coupled to one or more coil electrodes on one or more implantable medical leads. In the example of FIG. 1, IMD 16 is coupled to leads 18 and 22. IMD 16 may be, for example, an implantable pacemaker, cardioverter, and/or defibrillator that provides electrical signals to heart 12 via electrodes coupled to one or more of leads 18 and 22.

In the example of FIG. 1, leads 18 and 22 extend into the heart 12 to sense electrical activity of a heart 12 and/or deliver electrical therapy to heart 12. Right ventricular (RV) lead 18 extends through one or more veins (not shown), the superior vena cava (not shown), and right atrium 26, and into right ventricle 28. Right atrial (RA) lead 22 extends through one or more veins and the vena cava, and into the right atrium 26 of heart 12. Although example system 10 includes intravascular leads and intracardiac electrodes, extravascular leads including extravascular coil electrodes may include coil electrode assemblies according to the techniques of this disclosure.

IMD 16 may sense electrical signals attendant to the depolarization and repolarization of heart 12 via electrodes coupled to at least one of the leads 18 and 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria (including right atrium 26) and/or the ventricles (including right ventricle 28), and may also provide antitachyarrhythmia shocks, e.g., defibrillation and/or cardioversion shocks, via electrodes located on at least one of the leads 18 and 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

As shown in FIG. 1, the proximal ends of leads 18 and 22 are connected to a connector block 34 of IMD 16 to electrically couple the electrodes on the leads to circuitry within the housing 60 of IMD 16. In some examples, proximal ends of leads 18 and 22 may include electrical contacts that electrically couple to respective electrical contacts within connector block 34 of IMD 16. Each of the leads 18 and 22 includes an elongated insulative lead body, which may carry a number of conductors, e.g., a conductor for each electrode on the lead, each of which may be connected to a respective contact at the proximal end of the lead. Bipolar electrodes 40 and 42 are located adjacent to a distal end of lead 18 in right ventricle 28. In addition, bipolar electrodes 48 and 50 are located adjacent to a distal end of lead 22 in right atrium 26.

Electrodes 40 and 48 may take the form of ring electrodes, and electrodes 42 and 50 may take the form of helix tip electrodes mounted, e.g., with a fixed screw, within insulative electrode heads 52 and 56, respectively. Some helix tip electrodes can include a mechanism for an extendable/retractable helix. In other examples, one or more of electrodes 42 and 50 may take the form of small circular electrodes at the tip of a tined lead or other fixation element. Leads 18 and 22 also include elongated electrodes 62 and 66, respectively, each of which may take the form of a coil. Each of the electrodes 40, 42, 48, 50, 62 and 66 may be electrically coupled to a respective one of the conductors within the lead body of its associated lead 18 and 22, and thereby coupled to respective ones of the electrical contacts on the proximal end of leads 18 and 22.

In the example of FIG. 1, IMD 16 includes a housing electrode 58, which may be formed integrally with an outer surface of hermetically-sealed housing 60 of IMD 16, or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 48, 50, 62, and 66. The electrical signals are conducted to IMD 16 from the electrodes via the respective leads 18 and 22. IMD 16 may sense such electrical signals via any bipolar combination of electrodes 40, 42, 48, 50, 62, and 66. Furthermore, any of the electrodes 40, 42, 48, 50, 62, and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 48 and 50 to produce depolarization of cardiac tissue of heart 12. In some examples, IMD 16 delivers pacing pulses via any of electrodes 40, 42, 48 and 50 in combination with housing electrode 58 in a unipolar configuration. Furthermore, IMD 16 may deliver antitachyarrhythmia shocks, e.g., defibrillation shocks, to heart 12 via any combination of elongated electrodes 62 and 66, and housing electrode 58. IMD 16 may also use electrodes 58, 62, and 66 to deliver cardioversion shocks to heart 12. Electrodes 62 and 66 may be fabricated from any suitable electrically conductive material, such as, but not limited to, platinum, platinum alloy or other materials known to be usable in implantable defibrillation electrodes.

The configuration of system 10 illustrated in FIG. 1 is merely one example. In other examples, a system may include extravascular leads and electrodes instead of or in addition to the transvenous leads 18 and 22 illustrated in FIG. 1. Further, IMD 16 need not be implanted within the patient. In examples in which IMD 16 is not implanted in the patient, IMD 16 may sense electrical signals and/or deliver antitachyarrhythmia shocks and other therapies to heart 12 via percutaneous leads that extend through the skin of a patient to a variety of positions within or outside of heart 12.

Figure 2:
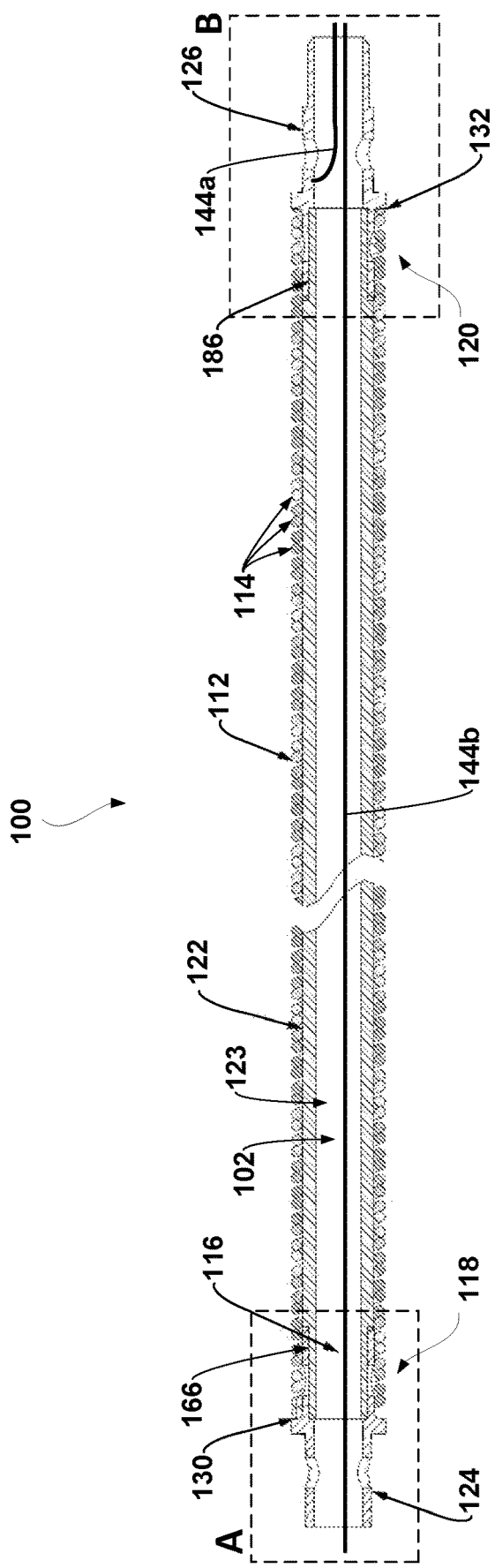
FIG. 2 is a cross-sectional diagram illustrating an example coil electrode assembly.
Figure 3:
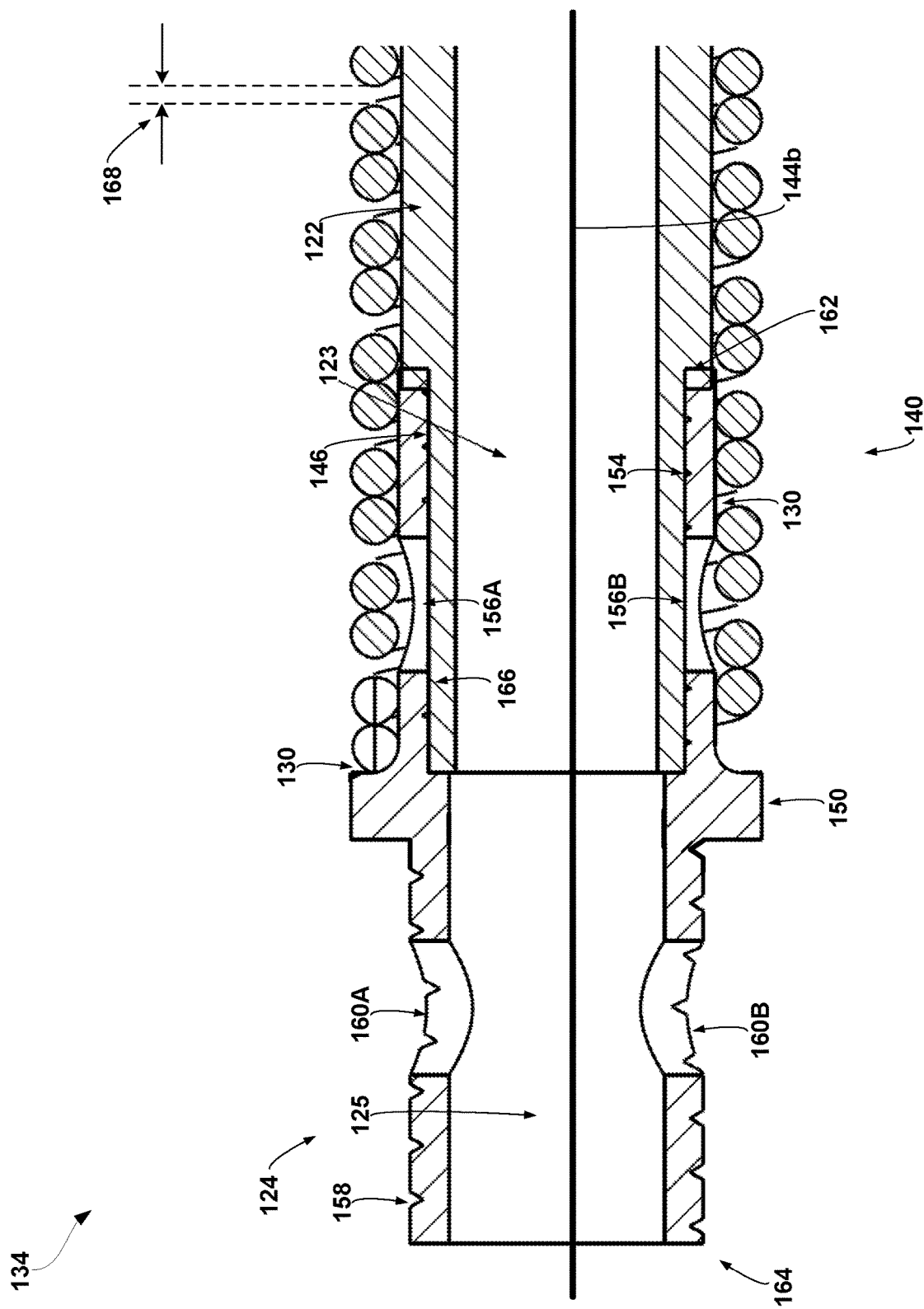
FIG. 3 is a cross-sectional diagram further illustrating a view of region A of a first end portion of the example coil electrode assembly of FIG. 2.
Figure 4:
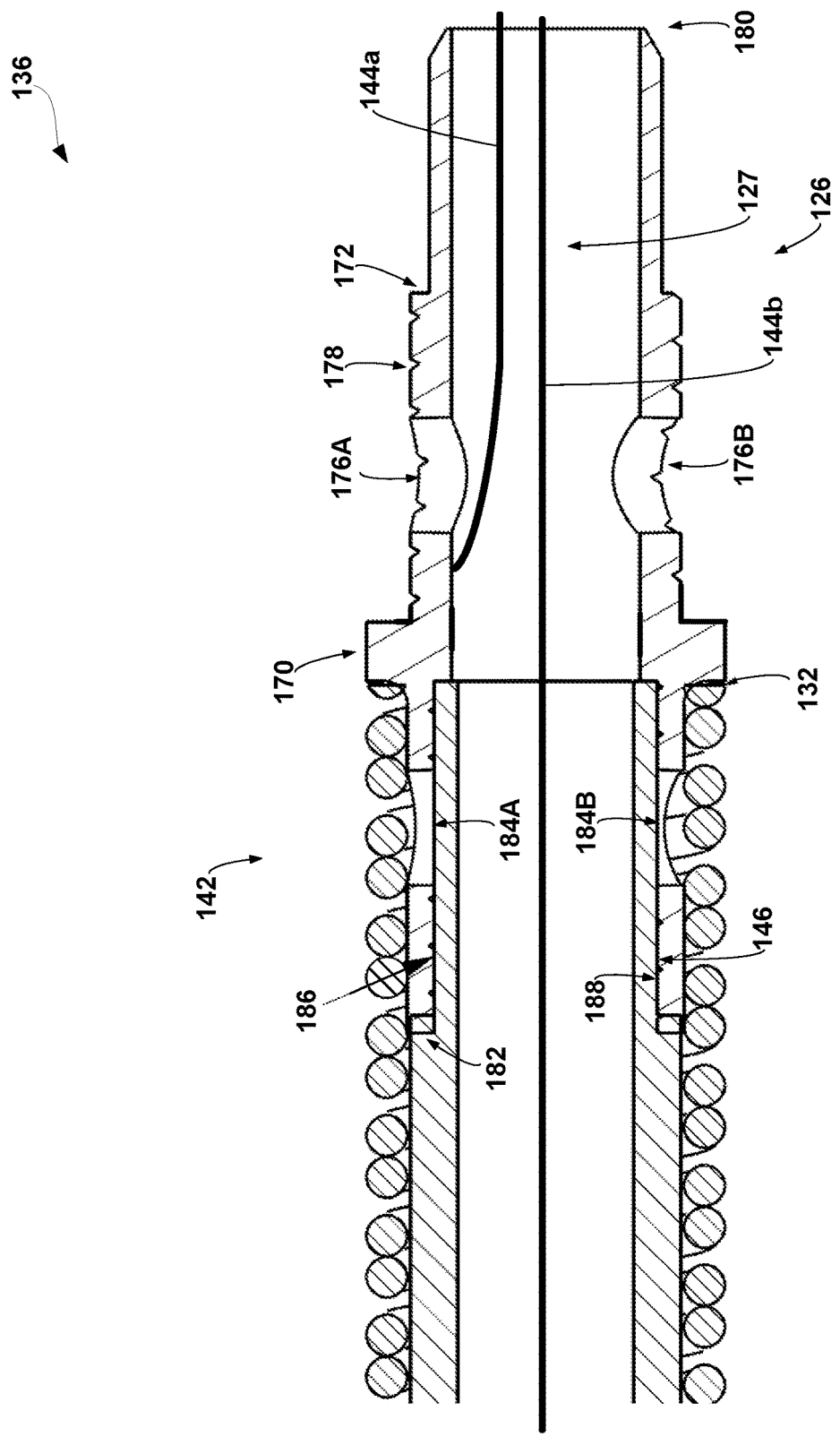
FIG. 4 is a cross-sectional diagram further illustrating a view of region B of a second end portion of the example coil electrode assembly of FIG. 2.
Figure 5:
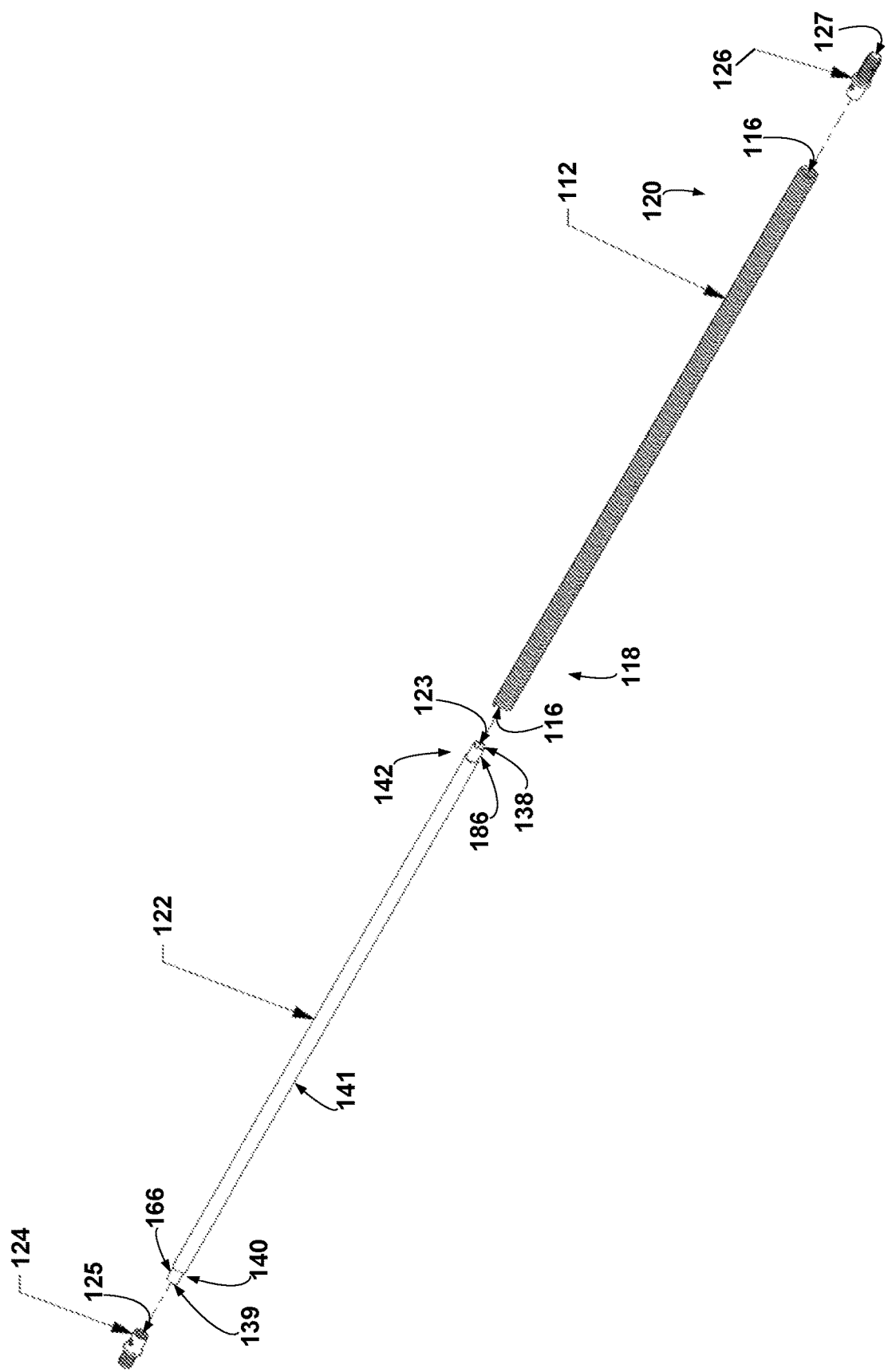
FIG. 5 is a conceptual diagram illustrating an exploded view of the example coil electrode assembly of FIG. 2.

FIG. 2 is a cross-sectional diagram that illustrates an example coil electrode assembly 100. FIG. 3 is a cross-sectional diagram that further illustrates a view of a first end portion 134 (region A from FIG. 2) of coil electrode assembly 100. FIG. 4 is a cross-sectional diagram that further illustrates a view of a second end portion 136 (region B from FIG. 2) of coil electrode assembly 100. FIG. 5 is a conceptual diagram illustrating an exploded view of the example coil electrode assembly of FIG. 2.

Coil electrode assembly 100 includes a coil electrode 112, an insulative tube 122, a first transition ring 124, and a second transition ring 126. When assembled as shown in FIG. 2, lumen respectively defined by each of insulative tube 122, first transition ring 124 and second transition ring 126 collectively define a lumen 102 of coil electrode assembly 100. Either or both of elongated electrodes 62 and 66 on leads 18 and 22, respectively, may be assembled according to the techniques described herein with respect to coil electrode assembly 100. In general, coil electrode assembly 100 may be included in an implantable medical lead at a desired position between a proximal end and a distal end of the lead.

Although inclusion on an implantable medical lead is described herein as an example, coil electrode assembly 100 can be used with other medical devices and/or therapies. In general, coil electrode assembly 100 can be used in any medical device or non-medical device.

In the example of FIG. 2, coil electrode 112 includes a plurality of windings 114 that extend from a coil electrode distal end 118 to a coil electrode proximal end 120. Windings 114 define a coil lumen 116 from a distal end 118 to a proximal end 120 of coil electrode 112. As shown in FIG. 5, insulative tube 122 extends from a tube proximal end 138 to a tube distal end 139. Insulative tube 122 extends within coil lumen 116, e.g., from the electrode distal end 118 to the electrode proximal end 120, such that coil electrode 112 extends along an outer surface 141 (FIG. 5) of insulative tube 122. When insulative tube 122 is in an expanded state to maintain a spacing 168 (as shown in FIG. 3) between windings 114, coil electrode 112 is partially embedded within insulative tube 122.

Insulative tube 122 may include a polymer including polyurethane and/or silicone. Inclusion of a polyurethane may provide desirable mechanical properties, such as relatively increased tensile and tear strength in at least the expanded state, compared to a similar thickness tube made from other materials. In some examples, the polymer or other material of insulative tube 122 may have a durometer hardness of at least 50 Shore D, such as approximately 55 Shore D.

First transition ring 124 is connected to coil electrode 112 at coil electrode distal end 118, and second transition ring 126 is connected to coil electrode 112 at coil electrode proximal end 120. In some examples, a first transition ring junction 130 defines a surface for the coil electrode to abut for the connection between first transition ring 124 and coil electrode 112, and a second transition ring junction 132 defines a surface for the coil electrode to abut for the connection between second transition ring 126 and coil electrode 112. The connection can be provided by multiple methods including welding, crimping, and staking, as examples. In some examples, each of first transition ring junction 130 and second transition ring junction 132 can withstand a tensile pull force of at least 1.0 pound.

First transition ring 124 defines an inner lumen 125 (FIGS. 3 and 5) and second transition ring 126 defines an inner lumen 127 (FIGS. 4 and 5). Insulative tube 122 defines an insulative tube lumen 123 (FIGS. 2 and 5). At least a portion of first transition ring 124 and second transition ring 126 are disposed within coil lumen 116, and in some examples between coil electrode 112 and an outer surface, e.g., outer surface 141 (FIG. 5), of insulative tube 122. Inner lumen 125 of first transition ring 124, insulative tube lumen 123, and inner lumen 127 of second transition ring 126 form lumen 102 of coil electrode assembly 100.

First transition ring 124 is connected to insulative tube 122 at tube distal end 139, and second transition ring 126 is connected to insulative tube 122 at tube proximal end 138. In some examples, a distal recess 166 (FIGS. 2, 3 and 5) is formed in a distal portion 140 (FIGS. 3 and 5) of insulative tube 122, and a proximal recess 186 (FIGS. 2, 4 and 5) in a proximal portion 142 (FIGS. 4 and 5) of insulative tube 122. Portions of first transition ring 124 and second transition ring 126 extending medially from junctions 130 and 132, respectively, can receive the portions of insulative tube 122 defining the respective one of the recesses 166 and 186. Distal recess 166 can help provide a secure fit between first transition ring 124 and insulative tube 122. Distal recess 166 and proximal recess 186 of insulative tube 122 can be reciprocally shaped to transition rings 124 and 126 so there is a substantially smooth transition from insulative tube 122 to transition rings 124 and 126. As illustrated in FIGS. 2-4, the combined thickness of insulative tube 122 at recesses 166 and 186 and the mated portions of transition rings 124 and 126 may define a substantially similar thickness to the thickness of the remainder of insulative tube 122.

In some examples, insulative tube 122 need not include recesses 166 and 186. Nevertheless, in such examples, distal portion 140 of insulative tube 122 including distal tube end 139 may be received within distal ring lumen 125, and proximal portion 142 of insulative tube 122 including proximal tube end 138 may be received within proximal ring lumen 127. An example of a coil electrode assembly in which an insulative tube does not include recesses at the distal and proximal portions is described with respect to FIGS. 6A-7B.

First transition ring 124 and second transition ring 126 may be made of a conductive material. In some examples, coil electrode assembly 100 can have one or more electrical conductors. A first electrical conductor 144a of an implantable medical lead (e.g., lead 18 or 22) may be electrically coupled to coil electrode 112 via at least one of the first transition ring 124 and second transition ring 126. In the example illustrated by FIG. 4, first electrical conductor 144a is coupled to second transition ring 126. First electrical conductor 144a may connect coil electrode 112, via transition ring 126 to the proximal end of the implantable medical lead.

In some examples, as shown in FIG. 2, a second conductors 144b may connect one or more electrodes distal of coil electrode assembly 100 to the proximal end of the implantable medical lead and, thus to the IMD (conductors 144a and 144b collectively as conductors 144). For example, with respect to the example of FIG. 2, second conductor 144b may extend through lumen 102 to connect electrodes 40 and 42 (or 48 and 50) to IMD 16 through coil electrode assembly 100 in which coil electrode 112 corresponds to electrode 62 and 66 (shown in FIG. 1).

As illustrated in FIG. 3, first transition ring 124 may include a proximal end 162 and a distal end 164. The proximal and distal sides extend from respective ends, 162 and 164, to an increased diameter shoulder 150. The proximal and distal sides of shoulder 150 can have different shapes and sizes. For example, proximal side of shoulder 150 can include a curved corner, and distal side of shoulder 150 can include a 90-degree (90°) corner. Proximal side of shoulder 150 provides first transition ring junction 130 which may include a surface for coil electrode 112 to engage. In some examples, coil electrode 112 may be welded to first transition ring 124 at proximal side of shoulder 150. Distal side of shoulder 150 provides a surface for coil electrode assembly 100 to connect with a remainder of a lead body of an implantable medical lead.

FIG. 4 is a conceptual diagram that illustrates an example proximal portion of coil electrode assembly 100 including second transition ring 126. Second transition ring 126 may be similar to first transition ring 124. In the illustrated example, second transition ring 126, with a proximal end 180 and a distal end 182, includes two increased diameter portions, defining a first shoulder 170 and a second shoulder 172. A distal side of shoulder 170 can include a curved corner, and proximal side of shoulder 170 can include an approximately 90-degree (90°) corner. Distal side of shoulder 170 provides second transition ring junction 132 which may include a surface for coil electrode 112 to engage. In some examples, coil electrode 112 may be welded to second transition ring 126 at proximal side of shoulder 170. In some examples, second shoulder 172 can provide a transition to the body of the implantable medical lead. Similar, to first transition ring 124, second transition ring 126 has holes 176A, 176B, 184A, 184B and grooves 178 and 188 to increase structural integrity of the joint by, e.g., adding additional locations/geometries for mechanical fixation of components. Similar to recess 166 at distal end of insulative tube 122, proximal end of insulative tube 122 also has a proximal recess 186 and functions to provide a connection between insulative tube 122 and second transition ring 126.

First transition ring 124 is connected to a distal portion 140 (FIG. 3) of insulative tube 122, and second transition ring 126 is connected to proximal portion 142 (FIG. 4) of insulative tube 122. Adhesive 146 is disposed on distal portion 140 of insulative tube 122 and proximal portion 142 of insulative tube 122, e.g., outer surface 141 of insulative tube 122 at these portions. Adhesive 146 connects first transition ring 124 to distal portion 140 of insulative tube 122 and second transition ring 126 to proximal portion 142 of insulative tube 122.

Adhesive 146 can be disposed in one location or multiple locations. In some examples, adhesive 146 is disposed only on two locations of insulative tube 122. The first location for adhesive 146 is located between a surface of first transition ring 124 and the distal portion 140 of insulative tube 122. The second location for adhesive 146 is between a surface of second transition ring 126 and the proximal portion 142 of insulative tube 122. In each location, adhesive 146 may be applied continuously or discontinuously as beads, a spray, parallel lines, or various patterns. For example, adhesive 146 can be applied in a continuous coating to the distal portion 140 of insulative tube 122 and applied in a discontinuous coating to the proximal portion 142 of insulative tube 122.

The amount of adhesive 146 applied to coil electrode assembly 100 may vary over a wide range. The composition of adhesive 146 can vary as well and can include silicone adhesive. In some examples, adhesive 146 can be a mixture of heptane and adhesive. Different compositions of adhesive 146 can be applied to different parts of insulative tube 122. For example, some portions of coil electrode assembly 100 may include a stronger adhesive 146 than other parts. In some examples, the connection of transition rings 124 and 126 to tube 122 may be by a variety of means in addition to or instead of adhesive 146.

Some areas of coil electrode assembly 100 can be free of adhesive 146. For example, an outer surface of coil electrode 112 may be substantially free of adhesive 146. At least part of first transition ring 124, a first area 145, can be free of adhesive 146. Similarly, at least part of second transition ring 126, a second area 147, can be free of adhesive 146. Both first transition ring 124 and second transition ring 126 can include multiple areas free of adhesive 146. By reducing the amount of adhesive 146 on the outer surface of coil electrode 112, the surface area of coil electrode 112 that is available to interact with the patient is increased, thereby potentially increasing the effectiveness of an implantable medical lead including coil electrode assembly 100.

Grooves 154 and holes 156A and 156B (collectively "holes 156") secure first transition ring 124 to insulative tube 122. Grooves 154 can facilitate connection with the use of adhesive. Holes 156 can also be used for inspection and verification. For example, holes 156 can be used to visually ensure insulative tube 122 is properly positioned in first transition ring 124. Holes 156A and 156B are on opposite sides of first transition ring 124. Holes 156 extend from outer surface of first transition ring 124 to inner lumen 125 of first transition ring 124. In some examples, instead of two holes 156A and 156B, there could be one hole or more than two holes 156. In some examples, multiple holes 156 could be placed circumferentially around first transition ring 124. Multiple holes 156 could be evenly or irregularly spaced. There could also be multiple holes 156 spaced longitudinally along first transition ring 124, instead of or in addition to holes 156 spaced circumferentially.

Grooves 154 can extend circumferentially around first transition ring 124. In some examples, grooves 154 may not extend completely circumferentially around first transition ring 124. For example, grooves 154 may extend only partially around the circumference of first transition ring 124. In addition, the angle of grooves 154 to the longitudinal axis of first transition ring 124 may vary. For example, grooves 154 may extend perpendicular or at an angle to a longitudinal axis of first transition ring 124.

Grooves 158 and holes 160A and 160B (collectively "holes 160") may be the same or substantially similar or different than grooves 154 and holes 156A and 156B. In some examples, grooves 154 and 158 may be substantially similar, and holes 156 may be different than holes 160, or vice versa. Grooves 158 and holes 160 provide connection means for first transition ring 124 and coil electrode assembly 100, respectively, to connect with other components and/or assemblies of the implantable medical lead. Grooves 158 can be used with adhesive to provide a connection between first transition ring 124 and a lead body. In some examples, grooves 158 can be used to promote an adhesive connection to other components, e.g., by increasing bond strength. Other connection means besides or in addition to grooves 154, 158 and holes 156, 160 could be used as well. Holes 156 and 160 can enable second conductor 144b to make an electrical connection from inner lumen 125 of first transition ring 124 to the exterior of first transition ring 124. Similar, to first transition ring 124, second transition ring 126 (FIG. 4) has holes 176A, 176B, 184A, 184B and grooves 178 and 188, which may provide substantially similar functionality to holes 156 and 160 and grooves 154 and 158 of first transition ring 124 (FIG. 3). In some examples, transition rings 124 and 126 can use holes 156, 160, 176, and 184 to promote adhesion to an attached component and provide an inspection/verification feature. In some examples, transition rings 124 and 126 may be free of holes 160 and 176.

FIGS. 6A and 6B are cross-sectional diagrams illustrating a pre-expansion state and a post-expansion state, respectively, of a region of another example coil electrode assembly similar to region A of the example coil electrode assembly of FIG. 2. First end portion 200 of FIGS. 6A and 6B is similar to first end portion 134, except for the differences described herein. For example, like first end portion 134, first end portion 200 includes a first transition ring 210, a coil electrode 224, and an insulative tube 226. First transition ring 210 is connected to a distal portion of a lead body 202. A conductor 208 extends through the middle of first end portion 200. A first insulator layer 206 and a second insulator layer 204 surround conductor 208. In some examples, first insulator layer 206 is a cable jacket, which can help protect conductor 208 from abrasion during or after assembly. In some examples, second insulator layer 204 is a tubing and can be made from any suitable insulative layer, such as, but not limited to, a polymer including polyurethane, silicone, or other materials known to be usable for insulative layers for conductors in medical applications.

In some examples, cable conductor 208 can be used as a pacing conductor, e.g., a cable conductor such as a stranded cable, and can be substantially similar to second conductor 144b. First transition ring 210 can be substantially similar to first transition ring 124. First transition ring 210 has grooves 216 and 222 and holes 212, 214, 218, and 220. Insulative tube 226 can be expanded so coil electrode 224 can be partially embedded within insulative tube 226, e.g., as shown in FIG. 6B, to maintain a spacing between the windings of coil electrode.

Unlike insulative tube 122 of FIG. 3, insulative tube 226 does not include a recess similar to distal recess 166 of first end portion 134. Instead, insulative tube 226 has a substantially uniform wall thickness along its entire length. Insulative tube 226 may require simpler manufacturing, e.g., fewer steps, then insulative tube 122 that includes recess 166. FIG. 6B shows insulative tube 226 in an expanded state such that coil electrode 224 is partially embedded within the post-expansion insulative tube 226.

FIGS. 7A and 7B are cross-sectional diagrams illustrating a pre-expansion state and a post-expansion state, respectively, of a region of the other example coil electrode assembly similar to region B of the example coil electrode assembly of FIG. 2. A second end portion 240 of FIGS. 7A and 7B is similar to second end portion 136 of FIG. 2, except for the differences described herein. For example, second end portion 240 includes insulative tube 226, coil electrode 224, second transition ring 250, a coil conductor 260, and a lead body 272. Conductor 208 is surrounded by a first insulator layer 206 and a second insulator layer 204.

In some examples, second transition ring 250 differs from second transition ring 126 of FIG. 2. For example, second transition ring 250 lacks a second shoulder. Further, grooves 258 can vary in size along a longitudinal length of second transition ring 250. For examples, grooves 258 on one portion of second transition ring 250 can be sized to promote an adhesive connection between second transition ring 250 and lead body 272. On a second, different portion of second transition ring 250 grooves 258 can be sized to provide connection between first transition ring 250 and coil conductor 260.

In a pre-expanded state, an inner diameter of an insulative tube may be substantially constant from the tube distal end to the tube proximal end, e.g., as illustrated with respect to insulative tube 226 in FIGS. 6A and 7A. In the expanded state, the inner diameter of the insulative tube may increase, e.g., at longitudinal positions where the tube is not constrained by the transition rings and expands into the electrode coil, as illustrated with respect to insulative tube 226 in FIGS. 6B and 7B. In some examples, in the expanded state, the inner diameter of the insulative tube at a center of the insulative tube is greater than the inner diameter of the insulative tube at the tube distal end and the tube proximal end.

Figure 8:
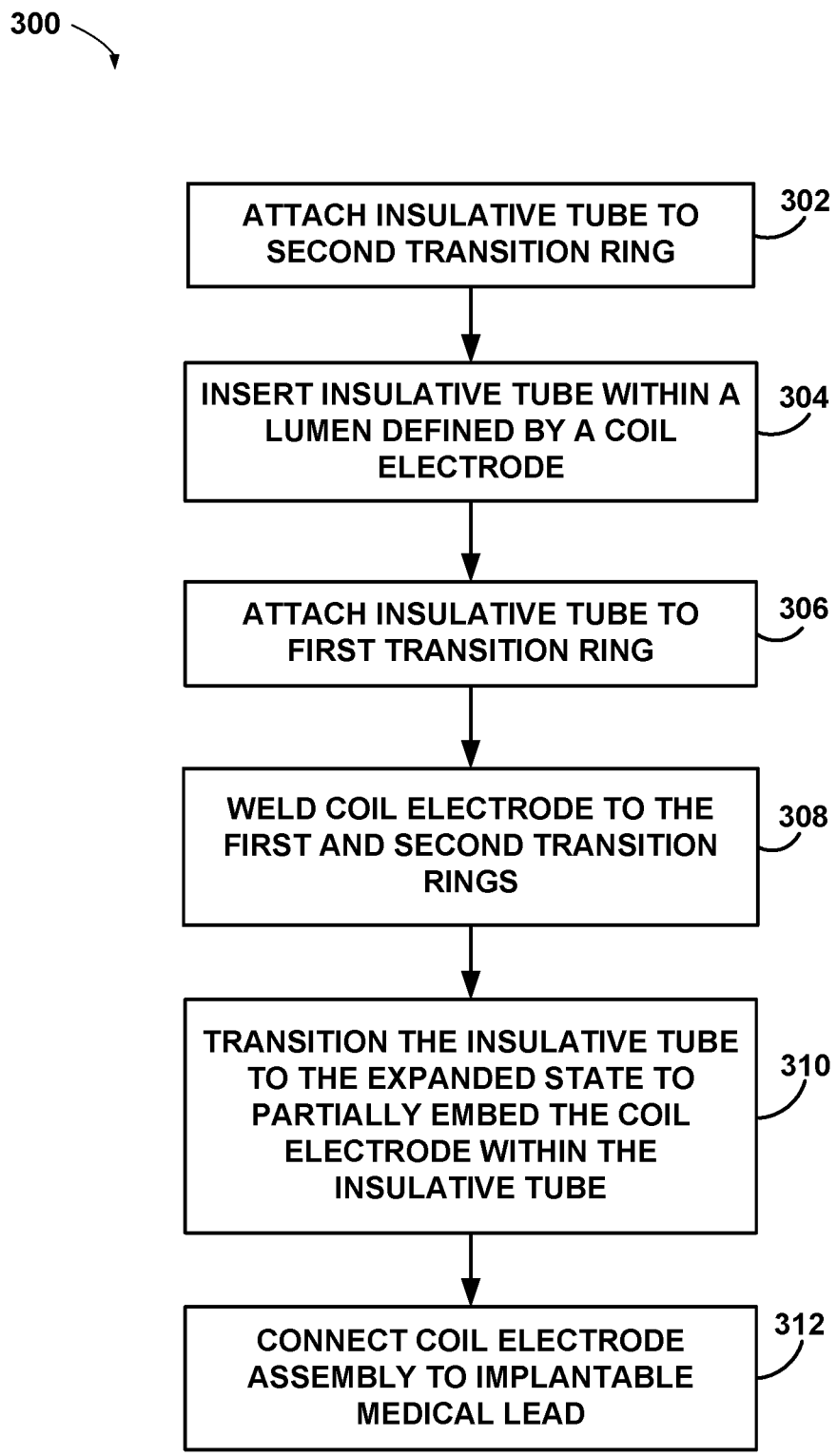
FIG. 8 is a flow diagram of an example technique for manufacturing a coil electrode assembly to be attached to an implantable medical lead.

FIG. 8 is a flow diagram of an example technique for manufacturing a coil electrode assembly 100 to be attached to an implantable medical lead. The technique of FIG. 8 will be described with concurrent reference to coil electrode assembly 100 (FIGS. 2-5) having a first end 134 (FIG. 3) and a second end 136 (FIG. 4), although a person having ordinary skill in the art will understand that the technique may be performed in reference to an electrode assembly having a first end 200 (FIGS. 6A and 6B) and a second end 240 (FIGS. 7A and 7B), another electrode assembly, another implantable medical lead, or any other medical device.

Method 200 of FIG. 8 includes attaching insulative tube 122 to second transition ring 126 (302). Insulative tube 122, with second transition ring 126 attached, is inserted within coil lumen 116 defined by windings 114 of coil electrode 112 (304). Insulative tube 122 is attached to first transition ring 124 (306). In some examples, insulative tube 122 is attached to first and second transition rings 124 and 126 with adhesive 146. Adhesive 146 can be applied along distal portion 140 and proximal portion 142 of the exterior surface of insulative tube 122. Adhesive 146 can also be applied to an exterior surface of insulative tube 122 before or after placement inside coil lumen 116. In some examples, instead of applying adhesive 146 to insulative tube 122, adhesive 146 can be applied to an internal surface of first and second transition rings 124 and 126.

In some examples, the order of steps 302, 304, and 306 can be rearranged without impacting the finished product (e.g., step 304 then steps 302 and 306). Steps 302, 304, and 306 may need to be completed before the steps welding and applying heat. For example, insulative tube 122 can be inserted into coil lumen 116 before attaching either first or second transition 124 and 126, e.g., switching steps 302 and 304. In some examples, steps 306 and 302 may also be switched.

Once insulative tube 122 is within coil lumen 116 defined by coil electrode 112 and first and second transition rings 124 and 126 are attached to insulative tube 122, coil electrode 122 is welded to first and second transition rings 124 and 126 (308). Insulative tube 122 can then be transitioned to the expanded state to partially embed coil electrode 112 within insulative tube 122 (310). Insulative tube 122 can be transitioned to the expanded state by application of heat and/or air (or other gas or liquid) pressure. The parameters of heat and/or air pressure may be selected to ensure insulative tube 122 does not rupture or overflow, or is otherwise damaged. Applying pressure may include applying air or another fluid or gas to an inside of insulative tube 122 over a range of between approximately 60 seconds to approximately 90 seconds at less than approximately 6900 Pascal (Pa) of internal pressure. Applying heat may include applying heat to insulative tube 122, e.g., the inside of the tube, over a range of between approximately 60 seconds to approximately 90 seconds at about 180 degrees Celsius (° C.). In one example, heat is applied to insulative tube 122 slowly for approximately 60 to 90 seconds at approximately 180° C., and internal pressure within insulative tube 122 is applied at a low pressure, such as less than 6900 Pa. In some examples, the heat and pressure are applied together and, more particularly, applied in the form of heated gas, e.g., air, delivered at a desired pressure, e.g., via a nozzle.

In some examples, based on predicted applications of coil electrode assembly 100 and material properties, different temperatures and/or pressures can be used to modify the expansion of insulative tube 122. After expanding insulative tube 122, an outer diameter of insulative tube 122 is less than an outer diameter of coil electrode 112. The temperature of insulative tube 122 is allowed to cool down after expansion. First and second transition rings 124 and 126 can be attached to a high-voltage conductor that extends within insulative tube 122. After coil electrode assembly 100 is complete, coil electrode assembly 100 can be attached to a lead, e.g., an implantable medical lead (312).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In addition, it should be noted that system described herein may not be limited to treatment of a human patient. In alternative examples, the system may be implemented in non-human patients, e.g., primates, canines, equines, pigs, and felines. These other animals may undergo clinical or research therapies that may benefit from the subject matter of this disclosure.

Various examples have been described. These and other examples are within the scope of the following claims.

What is claimed is:

1. An implantable medical lead configured to be coupled to an implantable medical device, the implantable medical lead comprising a coil electrode assembly, the coil electrode assembly comprising:
   a coil electrode extending from an electrode proximal end to an electrode distal end, the coil electrode defining an electrode lumen from the electrode proximal end to the electrode distal end, and the coil electrode comprising a plurality of windings;
   an insulative tube extending from a tube proximal end to a tube distal end, the insulative tube extending within the electrode lumen such that the coil electrode extends along an outer surface of the insulative tube, the coil electrode partially embedded within the insulative tube when the insulative tube is in an expanded state to maintain a spacing between the windings;
   a first transition ring at the electrode distal end and the tube distal end, wherein a portion of the first transition ring is within the electrode lumen, wherein the first transition ring defines a first transition ring lumen, and wherein a distal portion of the insulative tube including the tube distal end is within the first transition ring lumen; and
   a second transition ring at the electrode proximal end and the tube proximal end, wherein a portion of the second transition ring is within the electrode lumen, wherein the second transition ring defines a second transition ring lumen, and wherein a proximal portion of the insulative tube including the tube proximal end is within the second transition ring lumen.

2. The implantable medical lead of claim 1, further comprising an adhesive disposed on the distal portion of the insulative tube and the proximal portion of the insulative tube, wherein the adhesive is configured to connect the first transition ring to the distal portion of the insulative tube and the second transition ring to the proximal portion of the insulative tube.

3. The implantable medical lead of claim 2, wherein the adhesive is disposed on the insulative tube only between a surface of the first transition ring and the distal portion of the insulative tube and between a surface of the second transition ring and the proximal portion of the insulative tube.

4. The implantable medical lead of claim 2, wherein an outer surface of the coil electrode is substantially free of adhesive.

5. The implantable medical lead of claim 1, wherein each of the first and second transition rings is welded to the coil electrode.

6. The implantable medical lead of claim 1, wherein the insulative tube comprises a polymer and is configured to be transitioned to the expanded state by application of heat and air pressure.

7. The implantable medical lead of claim 6, wherein the polymer comprises polyurethane.

8. The implantable medical lead of claim 6, wherein the polymer has a durometer hardness of at least 50 Shore D.

9. The implantable medical lead of claim 1,
   wherein in a pre-expanded state, an inner diameter of the insulative tube is substantially constant from the tube distal end to the tube proximal end, and
   wherein in the expanded state, the inner diameter of the insulative tube at a center of the insulative tube is greater than the inner diameter of the insulative tube at the tube distal end and the tube proximal end.

10. A coil electrode assembly for an implantable medical lead configured to be coupled to an implantable medical device, the coil electrode assembly comprising:
    a coil electrode extending from an electrode proximal end to an electrode distal end, the coil electrode defining an electrode lumen from the electrode proximal end to the electrode distal end, and the coil electrode comprising a plurality of windings;
    an insulative tube extending from a tube proximal end to a tube distal end, the insulative tube extending within the electrode lumen such that the coil electrode extends along an outer surface of the insulative tube, the coil electrode partially embedded within the insulative tube when the insulative tube is in an expanded state to maintain a spacing between the windings;
    a first transition ring at the electrode distal end and the tube distal end, wherein a portion of the first transition ring is within the electrode lumen, wherein the first transition ring defines a first transition ring lumen, and wherein a distal portion of the insulative tube including the tube distal end is within the first transition ring lumen; and
    a second transition ring at the electrode proximal end and the tube proximal end, wherein a portion of the second transition ring is within the electrode lumen, wherein the second transition ring defines a second transition ring lumen, and wherein a proximal portion of the insulative tube including the tube proximal end is within the second transition ring lumen.

* * * * *